United States Patent [19]

McDermott et al.

[11] 4,052,515

[45] Oct. 4, 1977

[54] METHOD OF TREATING ACNE WITH ALCOHOL

[75] Inventors: James A. McDermott; Robert L. Anderson; Maurice E. Loomans, all of Cincinnati, Ohio

[73] Assignee: The Proctor & Gamble Company, Cincinnati, Ohio

[21] Appl. No.: 658,956

[22] Filed: Feb. 18, 1976

[51] Int. Cl.² ............................................. A61K 31/045
[52] U.S. Cl. .................................................... 424/343
[58] Field of Search ......................................... 424/343

[56] References Cited

U.S. PATENT DOCUMENTS

| 3,584,115 | 6/1971 | Gebhart | 424/343 X |
| 3,646,215 | 2/1972 | Phillips | 424/343 |
| 3,663,716 | 5/1972 | Stolar | 424/343 |
| 3,882,244 | 5/1975 | Lee | 424/343 |

FOREIGN PATENT DOCUMENTS

| 780,801 | 8/1957 | United Kingdom | 424/343 |

OTHER PUBLICATIONS

Drug & Cosmetic Industry, Apr. 1971, pp. 54, 56, 59, 134 to 138.

*Primary Examiner*—Dale R. Ore
*Attorney, Agent, or Firm*—Rose Ann Dabek; Julius P. Filcik; Richard C. Witte

[57] ABSTRACT

A composition containing a higher alcohol having from 6 to 12 carbon atoms and a lower alcohol is effective for treating acne when applied topically to affected areas.

9 Claims, No Drawings

METHOD OF TREATING ACNE WITH ALCOHOL

BACKGROUND OF THE INVENTION

This invention relates to a method of treating acne. More particularly, it relates to a method of topically treating acne with a composition containing a mixture of higher alcohols and lower alcohols.

Acne is a common inflammatory disease. It is characterized by the presence of comedones, inflammatory papules, pustules or cysts. The effects of acne vary from slight pitting to extremely disfiguring scars. It is commonly believed the presence of free fatty acids in the sebum is a primary cause of acne. These are produced principally by hydrolysis of sebum triglycerides and possibly by stearyl esters and/or wax esters by bacterial lipases, principally those of *Corynebacterium Acne* and/or lipases from an endogenous source. This event leads to rupture of the sebaceous duct of release of sebum or fat secretion and keratinaceous products into the skin instead of coming to the surface. The fatty acids are irritants to the tissue.

Various methods have been attempted for preventing the formation of acne and for treating it. Generally, such treatments have involved the topical application of various agents to the affected areas. Methods of treating acne have ranged from applying antibiotics to the affected areas to washing the affected areas with soap and water. U.S. Pat. No. 3,663,716, Stoler, May 16, 1972, suggests that acne can be controlled by the application of benzyl alcohol to the affected areas. The Stoler disclosure indicates that benzyl alcohol is effective in inhibiting the formation of free fatty acids and is, for this reason, an effective anti-acne agent. While various solutions to the problem of acne have been offered with varying degrees of success, there is still a need for an acne treatment which efficiently and effectively works.

It is an object of this invention to provide a method of treating acne.

It is another object of this invention to topically treat acne with a composition which is both efficacious and is not harmful to the treated areas.

It is still another object of this invention to topically apply to skin affected by acne a composition containing a mixture of alcohols.

These and other objects will become apparent from the description to follow.

As used herein, all percentages are by weight unless otherwise indicated.

SUMMARY OF THE INVENTION

A method of treating acne is provided which comprises applying to the skin area so affected an effective amount of a composition containing from 1 to 10% of a saturated or unsaturated higher alcohol having from 6 to 12 carbon atoms and the balance a lower alcohol selected from the group consisting of ethanol, propanol, isopropanol and mixtures thereof.

DESCRIPTION OF THE INVENTION

The present invention comprises topically applying to skin affected with acne a composition containing a mixture of alcohols. The composition contains a saturated or unsaturated higher alcohol having from 6 to 12 carbon atoms and the balance a lower alcohol having 2 or 3 carbon atoms. The essential components of this composition are further described in the following paragraphs.

The higher alcohol is the active anti-acne component of the hereindescribed compositions. The higher alcohols contain from 6 to 12 carbon atoms, preferably from 8 to 12 carbon atoms. The alcohol can be a saturated or unsaturated, primary or secondary alcohol. Preferably, the higher alcohol is a saturated primary alcohol. Examples of suitable higher alcohols include the following: 1-hexanol, 1-heptanol, 1-octanol, 1-nonanol, 1-decanol; 1-dodecanol, 2-octanol, 2-decanol, 4-octanol; 5-nonanol; 3-hexen-1-ol; 3-decen-1-ol; and 9-decen-1-ol.

Topical application of the higher alcohol, per se, to acne does not have a sufficiently noticeable effect on the alleviation of the acne. It has been found a lower alcohol must be included with the higher alcohol in order to obtain meaningful results. It is believed the presence of the lower alcohol facilitates the partitioning of the higher alcohol into the lipid phase of the sebum. An oil carrier or water is not able to deliver the higher alcohol to the area of the sebum where it can perform its function. The lower alcohol which has been found to aid the partitioning of the higher alcohol is selected from the group consisting of ethanol, propanol, isopropanol, and mixtures thereof. The preferred lower alcohol is ethanol.

The composition used in the method of this invention contains from 1 to 10%, preferably 3 to 8% of the higher alcohol with the balance the lower alcohol. Diluents such as water and propylene glycol can also be included in the compositions of this invention. Such compositions contain the same level of higher alcohol together with from 20 to 80%, preferably 40 to 60% of the lower alcohol and the balance a diluent such as the water or propylene glycol.

When treating acne it is preferred that a regimen involving multiple applications of the composition over a period of days or weeks be employed. The amount of the composition applied to the affected areas which constitutes an effective amount will vary depending on the particular person and degree of acne. It is preferred that the composition be applied to the affected areas at a rate of 3 milligrams of composition per square centimeter to 10 milligrams composition per square centimeter of treated tissue. The following examples illustrate this invention.

EXAMPLE I

Comedones are collected from the face of subjects with varying degrees of acne and homogenized in 0.05M phosphate buffer, pH 8.1. The mixture is centrifuged and the supernatant is used to measure lypolytic activity.

Cells of a pure culture of *Corynebacterium acne* are collected, lysed in 0.05M phosphate buffer and centrifuged. The resultant supernatant is also used to measure lypolytic activity.

Tributyrin (0.05%) is dispersed in the phosphate buffered solutions by sonication, the alcohol is added, and then an aliquot of the enzyme solution added. The decrease in turbidity is measured spectrophotometrically. Inhibitory activity is determined by comparing initial rates of change. Results obtained by using 1-octanol at two levels and 1-butanol are as follows.

| Alcohol | | Percent Inhibition | |
|---|---|---|---|
| | | C. Acne | Comedo Homogenate |
| 0.03% | 1-octanol | 63 | 20 |
| 0.1% | 1-octanol | 100 | 27 |

| | Percent Inhibition | |
|---|---|---|
| Alcohol | C. Acne | Comedo Homogenate |
| 0.1% 1-butanol | 0 | 0 |

The above results show that 1-octanol has a positive effect on inhibiting the hydrolysis of the tributyrin while the 1-butanol showed no measurable effect.

EXAMPLE II

Cells from three strains of *C.Acnes* and one strain of *Pityrosporum ovale* are collected and whole cells used to measure lipase activity. Tributyrin and triolein are used as substrates by dispersing them in a histidine-buffered system by sonication and measuring the acid changes with a pH stat. Alcohols are added to the substrate at a level of 0.5mMoles.

| | Percent Inhibition | |
|---|---|---|
| | 1-octanol | |
| Organism | Tributyrin | Triolein |
| P. Ovale | 60 | 12 |
| C. Acnes No. 4 | 63 | 100 |
| C. Acnes No. KS-5 | 33 | 76 |
| C. Acnes No. 10 | 52 | 88 |
| | 1-decanol | |
| P. Ovale | 63 | 24 |
| C. Acnes No. 4 | 55 | 43 |
| C. Acnes No. KS-5 | 43 | 83 |
| C. Acnes No. 10 | 40 | 46 |

The above results indicate the 1-octanol-and-decanol have broad inhibitory activity against different types and strains of skin microorganisms and substrates.

EXAMPLE III

A lipid mixture resembling human sebum in composition, but lacking free fatty acids, is applied to the back of guinea pigs along with an inoculum of *P. Ovale cells*. Alcohol is added to the artificial sebum lipid at concentrations of 1 and 5%. Irritation is graded after 5 days on a scale of 0–4, 4 being most severe. The results are as follows.

| | Average Irritation Grade | | |
|---|---|---|---|
| | Concentration of Alcohol in Artificial Sebum | | |
| Alcohol | 0 | 1.0% | 5.0% |
| 1-Octanol | 2.0 | 0 | 0.6 |
| 1-Decanol | 2.0 | 1.3 | 0.6 |
| 1-Dodecanol | 2.0 | 1.3 | 1.0 |

In a parallel experiment, 1-octanol is mixed in the artificial sebum in varying ratios. After 5 days the lipids are extracted and the quantity of free fatty acid determined.

| Alcohol Concentration | Irritation Grade | % Free Fatty Acids |
|---|---|---|
| 0 (Control) | 3 | 12.5 |
| 0.5 | 2 | 2.5 |
| 1.0 | 2 | 1.7 |
| 5.0 | 0.5 | 2.5 |

These results show the 1-octanol,-decanol and -dodecanol are able to reduce the irritation produced by the mixture of *P. Ovale* cells and artificial sebum lipid and is correlated to the amount of free fatty acid produced by this mixture.

EXAMPLE IV

The following compositions are formulated.

| Component | A | B | C | D | E |
|---|---|---|---|---|---|
| 1-octanol | 3% | 3% | 6% | 2% | 8 |
| Ethanol | 48.5% | 48.5% | 40% | 98% | 46% |
| Water | 48.5% | — | — | — | 46% |
| Propylene glycol | — | 48.5% | 54% | — | — |

The above compositions show an anti-acne effect when topically applied to skin areas so affected at a rate of between 3 to 10 milligrams composition per square centimeter of skin over a period of about 3 weeks.

Substitution of 1-decanol, 1-dodecanol, 2-octanol, 3-decen-1-ol and 3-hexen-1-ol for the 1-octanol in the above compositions gives substantially the same results.

Propanol or isopropanol used in place of the ethanol of the compositions above also gives substantially the same results

What is claimed is:

1. A method of treating acne comprising applying to the skin areas so affected from 3 milligrams per square centimeter to 10 milligrams per square centimeter of a composition containing from 1 to 10% of a saturated or unsaturated higher alcohol having from 6 to 12 carbon atoms and the balance a lower alcohol selected from the group consisting of ethanol, propanol, ispropanol and mixtures thereof.

2. The method of claim 1 wherein the lower alcohol represents from 20 to 80% of the composition and the balance comprises water.

3. The method of claim 1 wherein the lower alcohol represents from 20 to 80% of the composition and the balance comprises propylene glycol.

4. The method of claim 2 wherein the lower alcohol represents from 40 to 60% of the composition.

5. The method of claim 3 wherein the lower alcohol represents from 50 to 60% of the composition.

6. The method of claim 1 wherein the higher alcohol is saturated.

7. The method of claim 6 wherein the higher alcohol represents from 3 to 8% of the composition.

8. The method of claim 7 wherein the higher alcohol has from 8 to 12 carbon atoms.

9. The method of claim 8 wherein the higher alcohol is 1-octanol.